(12) United States Patent
Isogai et al.

(10) Patent No.: US 7,824,032 B2
(45) Date of Patent: Nov. 2, 2010

(54) EYE REFRACTIVE POWER MEASUREMENT APPARATUS

(75) Inventors: Naoki Isogai, Nishio (JP); Masaaki Hanebuchi, Nukata-gun (JP); Mitsuhiro Gono, Nukata-gun (JP); Kenji Nakamura, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 274 days.

(21) Appl. No.: 11/813,553

(22) PCT Filed: Jan. 6, 2006

(86) PCT No.: PCT/JP2006/300116

§ 371 (c)(1),
(2), (4) Date: Nov. 4, 2008

(87) PCT Pub. No.: WO2006/073196

PCT Pub. Date: Jul. 13, 2006

(65) Prior Publication Data

US 2009/0185136 A1   Jul. 23, 2009

(30) Foreign Application Priority Data

Jan. 7, 2005 (JP) ............................. 2005-002060
Jan. 7, 2005 (JP) ............................. 2005-002061

(51) Int. Cl.
*A61B 3/08* (2006.01)
*A61B 3/10* (2006.01)
(52) U.S. Cl. .................. 351/202; 351/205; 351/221
(58) Field of Classification Search ............. 351/200, 351/202, 205–206, 212, 221
See application file for complete search history.

(56) References Cited

U.S. PATENT DOCUMENTS

| 7,275,828 | B2 * | 10/2007 | Imaizumi ................. 351/212 |
| 7,316,480 | B2 * | 1/2008 | Hanebuchi et al. .......... 351/211 |
| 7,416,301 | B2 * | 8/2008 | Hanebuchi et al. .......... 351/205 |
| 2005/0157261 | A1 | 7/2005 | Hanebuchi et al. | |

FOREIGN PATENT DOCUMENTS

| JP | 01-293841 A | 11/1989 |
| JP | 09-253052 A | 9/1997 |

(Continued)

OTHER PUBLICATIONS

Notification of Reasons for Refusal issued Jul. 28, 2010 in counterpart Japanese Application No. 2005-002061.

*Primary Examiner*—Scott J Sugarman
*Assistant Examiner*—Dawayne A Pinkney
(74) *Attorney, Agent, or Firm*—Sughrue Mion, PLLC (57) ABSTRACT

An eye refractive power measurement apparatus for objectively measuring eye refractive power of a patient's eye, includes: a light-projecting optical system that includes a light source and projects measurement light onto a fundus of the patient's eye; a light-receiving optical system that includes an imager device serving as a two-dimensional light-receiving element and receives the measurement light reflected from the fundus; and an operating section that determines the eye refractive power of the eye based on a two-dimensional pattern image by the measurement light imaged by the imager device. The light source is a super-luminescent diode or a laser diode that emits light having a center wavelength in a range of approximately 850 nm to 940 nm.

7 Claims, 6 Drawing Sheets

FOREIGN PATENT DOCUMENTS

| | | |
|---|---|---|
| JP | 10-71122 A | 3/1998 |
| JP | 10-94516 A | 4/1998 |
| JP | 2002-306416 A | 10/2002 |
| JP | 2002-345753 A | 12/2002 |
| JP | 2004-290287 A | 10/2004 |

* cited by examiner

EYE REFRACTIVE POWER MEASUREMENT APPARATUS

TECHNICAL FIELD

The present invention relates to an eye refractive power measurement apparatus that objectively measures eye refractive power of a patient's eye.

BACKGROUND ART

There is known, an apparatus that projects measurement light onto a fundus of a patient's eye, receives the measurement light reflected, therefrom by a two-dimensional light-receiving element, and measures eye refractive power of the patient's eye based on the result of the light reception (detection result). In such, an apparatus, an infrared light-emitting diode (LED) is usually used as a light source (measurement light source) for projecting measurement light.

In the meanwhile, the light source and the light-receiving element are arranged in positions conjugate with the fundus (e.g. with the fundus of an emmetropic eye). Where the LED is used as the light source, measuring accuracy is problematically worsened by luminance decrease, light noise effect and the like because it is greater in size as a light source and the luminous flux of measurement light is greater in diameter.

Meanwhile, because of absorption of the measurement light and attenuation of its reflection light, there is a difficulty in obtaining a sufficient light-amount at the light-receiving element. Particularly, as for infrared light, there is a problem of light-amount deficiency because light-receiving sensitivity is considerably low at the light-receiving element.

It is a technical problem of the present invention to provide an eye refractive power measurement apparatus capable of accurately obtaining a measurement result, in view of the problem as encountered in the prior art.

DISCLOSURE OF THE INVENTION

The present invention is characterized by the following structure, in order to solve the problem.

An eye refractive power measurement apparatus for objectively measuring, eye refractive power of a patient's eye, comprising:

a light-projecting optical system that includes a light source and projects measurement light onto a fundus of the patient's eye;

a light-receiving, optical system that includes an imager device serving as a two-dimensional light-receiving element and receives the measurement light reflected from the fundus; and an operating section that determines the eye refractive power of the eye based on a two-dimensional pattern image by the measurement light imaged by the imager device, wherein the light source is a super-luminescent diode or a laser diode that emits light having a center wavelength in a range of approximately 850 nm to 940 nm.

BEST MODE FOR CARRYING OUT THE INVENTION

Figure 1:
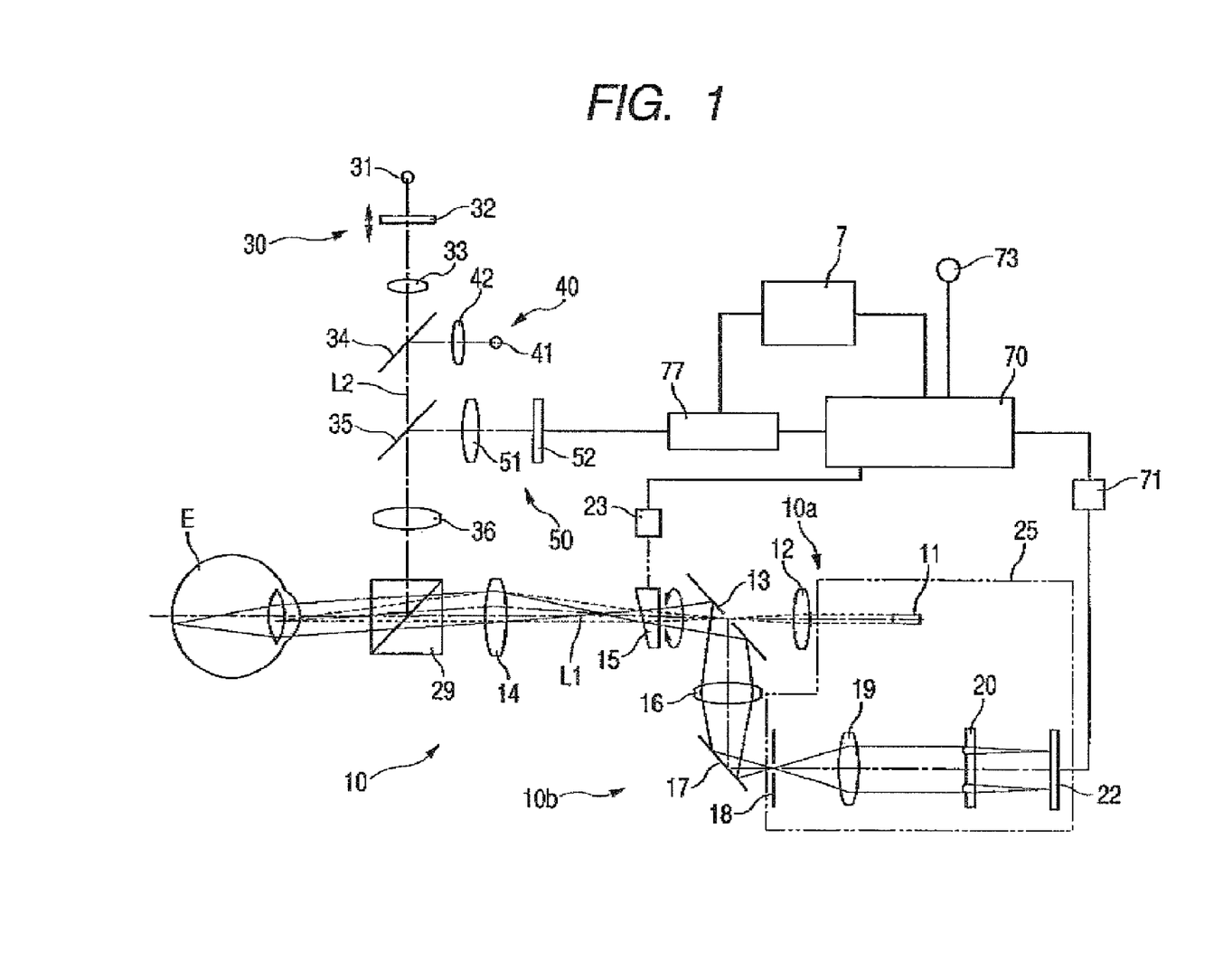
FIG. 1 is a schematic construction diagram of an optical system and a control system of an eye refractive power measurement apparatus according to a present embodiment.

Referring to the drawings, explanation will now be made on an embodiment according to the present invention. FIG. 1 is a schematic construction diagram of an optical system and a control system of an eye refractive power measurement apparatus according to a present embodiment. A measurement optical system 10 includes a light-projecting optical system 10a that projects a spot-shaped measurement light onto a fundus of a patient's eye E through a pupil center thereof, and a light-receiving optical system 10b that receives the measurement light reflected from the fundus in a ring form from a pupil periphery. The light-projecting optical system 10a includes, on a measurement optical axis L1, a light source 11, relay lens 12, a hole mirror 13, a prism 15 rotating about the optical axis L1 by means of a rotating section 23, and an objective lens 14.

The light source 11, used in the embodiment, employs a super-luminescence diode (SLD) to emit light having an infrared region. The SLD having a center wavelength of 850 nm or greater and 940 nm or smaller can be suitably used, the SLD having a center wavelength of 870 nm or greater and 900 nm or smaller can be more suitably used. At a center wavelength smaller than 850 nm, visual perception can be done during measurement, which makes it difficult to perform fogging of the eye E during the measurement and hence has a bad effect upon measurement accuracy. Meanwhile, at a center wavelength greater than 940 nm, absorption is greater in a crystalline lens, a vitreous body, etc., to reduce the measurement light to the fundus and the reflection light from the fundus, thus making it difficult to secure a required light-amount for the measurement. Incidentally, the embodiment uses the SLD as a highly-directive light source 11. However, it is not limitative, i.e. a laser diode (LD) or the like is usable.

The light source 11 is in a conjugate relationship with the fundus while the hole mirror 13 at its hole region is in a conjugate relationship with the pupil. The prism 15, provided on the common optical path of the light-projecting and light-receiving optical systems 10a and 10b, is arranged in a position off the conjugate position with the fundus. The prism 15 causes the traveling light to eccentrically rotate relative to the optical axis L1, in order to suppress the speckle noise occurring by the use of a coherent light source. By passing the reflection light from the fundus through the same prism 15 that is common to the light-projecting optical system 10a, it behaves as if there were no eccentricity, at the pupil, in the projection/reflection (reception) light over the subsequent optical system. Incidentally, in place of the prism 15, a parallel-surfaced plate may be arranged obliquely on the optical axis L1. A beam splitter 29 is arranged between the objective lens 14 and the eye E.

The light-receiving optical system 10b uses the objective lens 14, the prism 15 and the hole mirror 13 commonly to the light-projecting optical system 10a, and includes a relay lens 16 and a total reflection mirror 17 arranged on an optical path along the reflection upon the Hole mirror 13, a diaphragm 18 arranged on an optical path along the reflection upon the mirror 17, a collimator lens 19, a ring lens 20 arranged in a conjugate relationship with the pupil, and an imager device 22 serving as a two-dimensional light-receiving device such as an area CCD. The diaphragm 18 and the imager device 22 are in a conjugate relationship with the fundus. The imager device 22 is connected to an operation control section 70 through a frame memory 71.

Figure 2A:
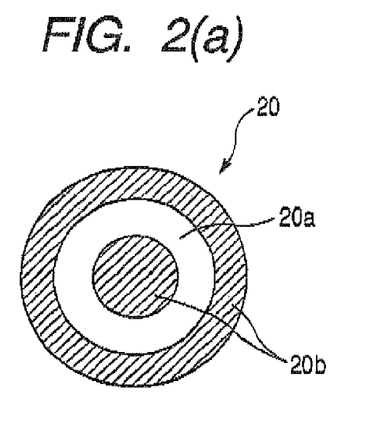
FIG. 2 is a schematic structural view of a ring lens.
Figure 2B:
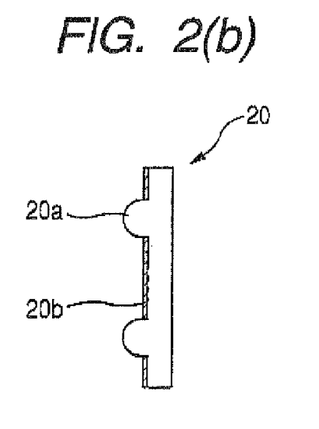

The ring lens 20 is structured with a lens region 20a forming a cylindrical lens in a ring form on a plate and a shade region 20b applied with coating, for shading, over an area other than the lens region 20a, as shown in FIGS. 2A and 2B. This focuses a ring-pattern image on the imager device 22 arranged at the focal point thereof. Although in the embodiment the imager device 22 is farmed to receive a ring-pattern image through the ring lens 20, an optical system in which the imager device 22 receives a two-dimensional pattern image by a Hartman-Shack plate structured with micro-lenses in a matrix form or a 6-port (pinhole) diaphragm and a polarization prism may be used as the light-receiving optical system.

An objective lens 36, a half mirror 35, a dichroic mirror 34, a projection lens 33, a fixation target 32 and a visible-light source 31 are arranged in the order on an optical axis L2 coaxially with the optical axis L1 through the beam splitter 29. A fixation target optical system 30 is configured by the elements of between the light source 31 and the objective lens 36. The fixation target 32 is to perform fogging of the eye E by being moved over the optical axis L2. The light source 31 illuminates the fixation target 32 so that the light from the fixation target 32 can travel through the lens 33, the dichroic mirror 34, the half mirror 35 and the objective lens 36, thus being reflected by the beam splitter 29 toward the eye E. On the opposite side of the dichroic mirror 34, an alignment optical system 40 is provided which has an alignment light source 41 to emit infrared light and a projection lens 42. The light from the light source 41 projects an alignment target onto the cornea of the eye E through the projection lens 42 and the dichroic mirror 34 to the beam splitter 29.

An imaging lens 51 and an imager device 52, such as an area CCD, for observing an anterior segment of the eye E are arranged on the opposite side of the half mirror 35, thus constituting an observation optical system 50. The reflection light from the anterior segment including the alignment target is reflected by the beam-splitter 29, passes through the lens 36, the half mirror 35 and the imaging lens 51, and is received at the imager device 52. An output of the imager device 52 is connected through an image processing section 77 to a monitor 7 on which an observation image is displayed.

Now explanation is made on the operation of the apparatus constructed as above. In measurement, an operator aligns the apparatus with the eye E shown in FIG. 1 by operating a not-shown joystick, based on an anterior segment image and an alignment target image displayed on the monitor 7. After the eye E is prompted to gaze the fixation target 32 and the apparatus is properly aligned with the eye E, a measurement start switch 73 is pressed to start the measurement.

The operation control section 70 turns on the light source 11 and rotates the prism 15 at high speed by means of the rotating section 23 based on the measurement start signal from the switch 73. A preparatory measurement, for performing fogging of the eye E, is performed and the fixation target 32 is put in a conjugate position with the fundus depending upon the refractive power obtained. Then, the control section 70 moves the fixation target 32 such that fogging is made in a suitable amount of diopter. Therefore, a main measurement can be performed in the state the eye E is fogged.

Incidentally, when the measurement light from the light source 11 can be viewed in a somewhat degree when the fogging is performed, color arrangement can be determined in such a manner that the color of the measurement light is assimilated with the fixation target 32. For example, the fixation target 32 may be made in a red-based color.

The infrared light from the light source 11 travels through the lens 12, the hole region of the hole mirror 13, the prism 15, the lens 14 and the beam splitter 29, to form a point light-source image on the fundus of the eye E. At this time, the pupil projection image (projection light on the pupil) is eccentrically rotated at high speed on the hole region of the hole mirror 13 by the prism IS rotating about the optical axis L1.

The point light-source image projected on the fundus is reflected/scattered and then passed through the beam splitter 29 and collected by the lens 14, again collected to the position of the diaphragm 18 through the prism 15 rotating at high speed, the hole mirror 13, the lens 16 and the mirror 17, and is focused in a ring form, on the imager device 22 by the collimator lens 19 and ring lens 20. The output signal from the imager device 22 is stored as image data in the frame memory 71. In the case the eye E is an emmetropic eye, the reflection light from, the fundus is incident as collimated light upon the ring lens 20 so that a ring-pattern image in the same size as the ring lens 20 is focused on the imaging device 22. Meanwhile, when the eye E is abnormal in its spherical refractive component, a ring-pattern image on the imager device 22 has a diameter in a size proportional to the amount of the spherical refractive error (smaller for the near-sighted eye while greater for the far-sighted eye). In the case there is an astigmatic refractive error, a ring-pattern image is formed elliptic on the imager device 22 in accordance with the astigmatic refractive error. Accordingly, the control section 70 can determine a meridional refractive error by detecting the meridional position of the ring pattern image depending upon the image data stored in the frame memory 71. By performing a predetermined process on it, a refractive value can be determined as to S (spherical power), C (astigmatic (cylindrical) power) and A (astigmatic axis angle). Incidentally, the position of the ring-pattern image can be detected from a center of edges of the ring-pattern image, a center-of-gravity of luminance level, a peak of light amount level, or the like. Meanwhile, the light source 11, the diaphragm 18, the lens 19, the ring lens 20 and the imager device 22 may be made so as to be integrally movable, and refractive power may be obtained based on the movement amount of the light source 11 and imager device 22 up to a conjugation with the fundus and the form of the ring-pattern image.

Meanwhile, when the prism 15a is not employed and a light source having high luminance and high coherence like the SLD is used, speckle noise occurs in the ring-pattern image received at the imager device 22 due to the scatter within the eye E and the ring-pattern image is speckled in its light-amount distribution. However, because this embodiment has a structure (with high-speed rotation of the prism 15) to eccentrically rotate the point light (point light source image) projected on the fundus, the speckle noise caused upon using the coherent light source (SLD) is neutralized during imaging at the imager device 22, thus making it possible to eliminate the effect thereof.

Incidentally, the SLD is smaller in light-source size but higher in directivity as compared to the LED, thus realizing a smaller diameter of measurement light. Therefore, because a smaller spot image is projected on the fundus with less scatter at various points within the eye E, the image device 22 for receiving the reflection light thereof is allowed to take a sharp image of a thin ring pattern with less noise. The spot image projected on the fundus is approximately 50 μm or greater in diameter for the LED as compared to that of approximately 10 μm or greater in diameter for the SLD. When an LED is used as a measurement light source, a ring pattern image having a thick ring width is imaged with a large quantity of flare components at around thereof. Namely, as compared to the apparatus using an LED as a measurement light source, the apparatus in the present embodiment is allowed to determine refractive power based on a sharp ring pattern image with less noise, thus obtaining an accurate measurement result with less measurement errors.

Incidentally, in the case that the measurement light source 11 uses a light source that is small in size but high in directivity, such as an SLD or an LD, if a center wavelength is approximately 830 nm, measurement light is to be easily viewed. For this reason, a longer wavelength of light is preferably used. However, as shifted toward the longer wavelength, wavelength sensitivity lowers at the imager device 22. Accordingly, in order to enhance the measurement accuracy furthermore, there is a need to set an imaging gain of the image device 22 with taking account of the wavelength range of the measurement light source 11 and the wavelength sensitivity characteristic at the imager device 22.

Now explanation is made on the setting of the imaging gain on the imager device 22 of the present embodiment.

Figure 3:
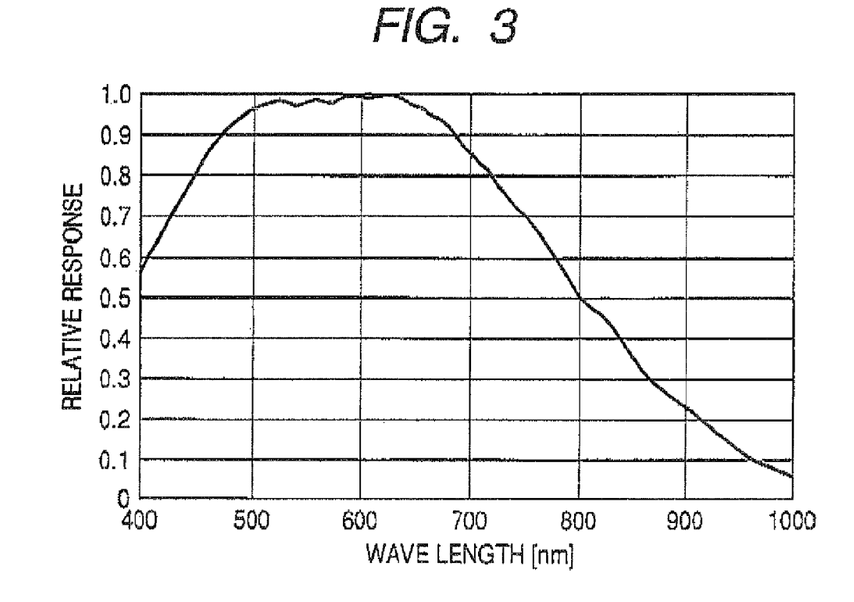
FIG. 3 is an example for explaining a wavelength sensitivity characteristic of an imager device.

For example, when using an imaging device having a characteristic shown in FIG. 3, sensitivity is lower by approximately 40% at 875 nm of light as compared to an 875 nm of light. Namely, when the measurement light source 11 uses an SLD at 875 nm, the optical signal detected at the imager device 22 has luminance lowered 40% in level. As a result, the resulting ring pattern image is wholly dark. It can be considered to simply increase the imaging gain at the imager device by an amount of sensitivity-decrease (e.g. the imaging gain may be increased by approximately 1.7 times for a light amount lower of 40% in level). However, it has been found that, in case eye measurement is made by simply increasing the imaging gain correspondingly to the deficient amount of light, required amount of light is obtainable but light noise (scattering, and reflecting portions of light in the crystalline lens, the vitreous body, etc. of the eye) increases upon detection. More specifically there is a tendency of noise component increase at the inner region rather than the pouter region of the ring pattern image. By the affect of such a noise component, there encounters a shift of the resulting refractive power toward minus (toward the near-sighted vision) from the value in nature.

Figure 4A:
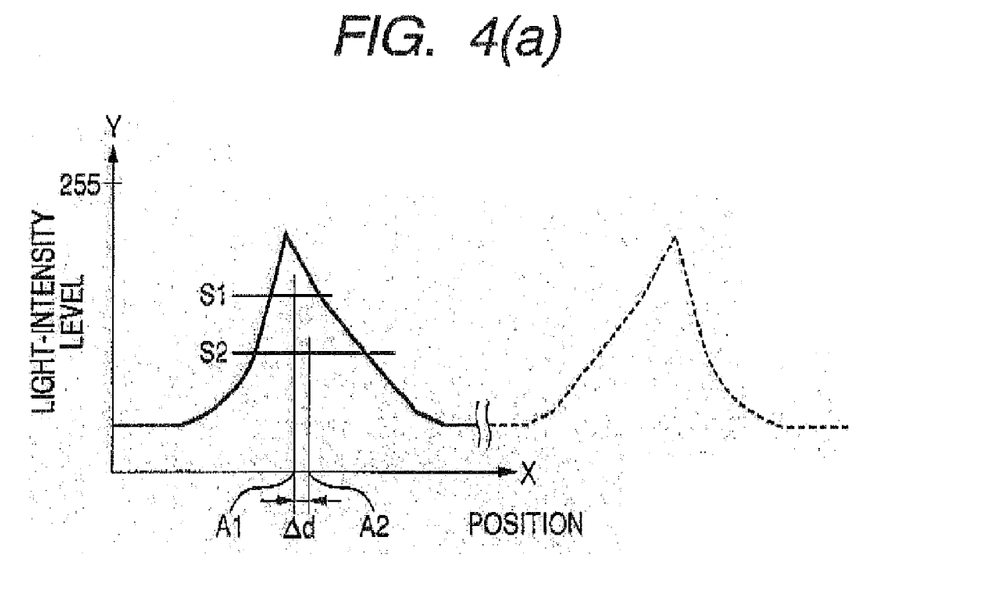
FIG. 4 is a drawing showing a part of an optical-signal luminance level waveform in a predetermined meridional direction.

FIG. 4A shows a part of a luminance level waveform of an optical signal in a predetermined meridional direction, in a ring pattern image containing a greater amount of noise components (in which a position is represented on the X axis while luminance level is on the Y axis). In this case, the waveform is asymmetric left and right and moderately slanted (edges slackened). If detecting the position of the ring-pattern image based on such a waveform, measurement errors easily occur under the influence of noises. For example, in case the resulting waveform is cut at the threshold S and detection is made by taking an intermediate of the waveform at the cut position as an image position, if the waveform is asymmetric left and right, then the image detecting position (A1, A2) vary depending upon the setting levels (S1, S2) of the threshold S. Meanwhile, the decrease of waveform inclination and the luminance level width increase at the threshold S also constitute a factor to increase the measurement errors.

Figure 4B:
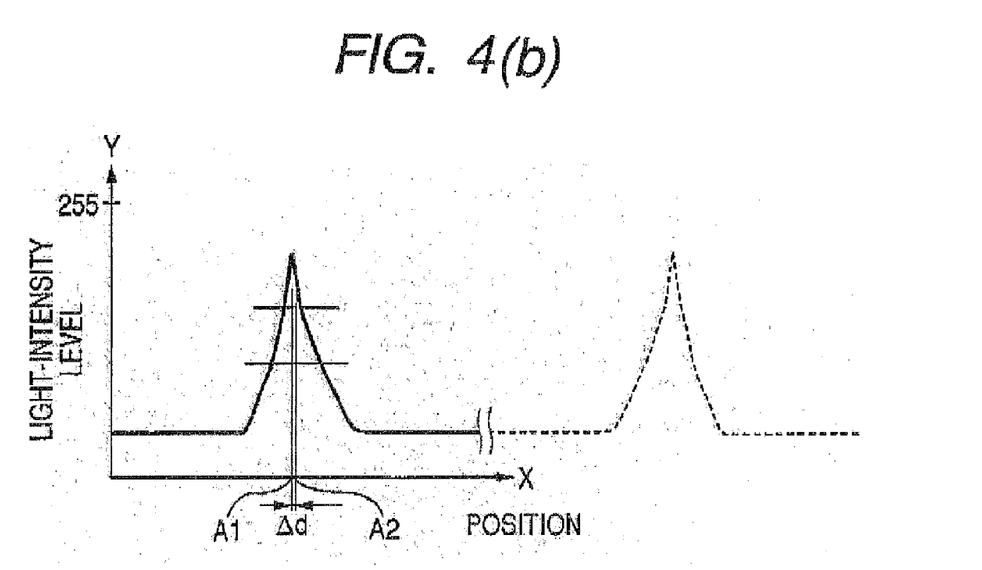

Accordingly, in order to suppress the noise-component light signal contained in a two-dimensional pattern image received at the imager device 22 while securing the light signal intensity required, the imaging gain of the imaging device 22 is adjusted (established) based on the wavelength range at the light source 11 and the wavelength sensitivity characteristic at the imager device 22. For example, the imaging gain of the imager device 22 is adjusted depending upon whether or not the intensity-level waveform of the optical signal is nearly symmetric left and right as shown in FIG. 4B upon detecting the position of the ring-pattern image. In this case, a range where the optical-signal luminance level waveform assumes symmetric left and right on the border of its peak can be set while changing the imaging gain of the imager device 22. In determining a waveform symmetry in left and right, there can be considered a method that two thresholds S1, S2 are set up for the waveform so that determination is made depending upon, whether or not the deviation Δd between the positions A1, A2 which are image positions of the Intermediates of the waveforms obtained by the established thresholds S1, S2 fails within an acceptable range. By thus adjusting the imaging gain in a manner to obtain a waveform satisfying a predetermined criterion, by detecting the image position, from the luminance level waveform of the optical signal less susceptible to the effect of light noise, the measurement accuracy furthermore is improved. Incidentally, when the two-dimensional pattern image received at the imager device 22 is the ring-pattern image as in the present embodiment, in setting of the imaging gain of the imager device 22 may be adjusted in a manner suppressing the noise component occurring in the two-dimensional pattern image at its inner region.

Figure 5:
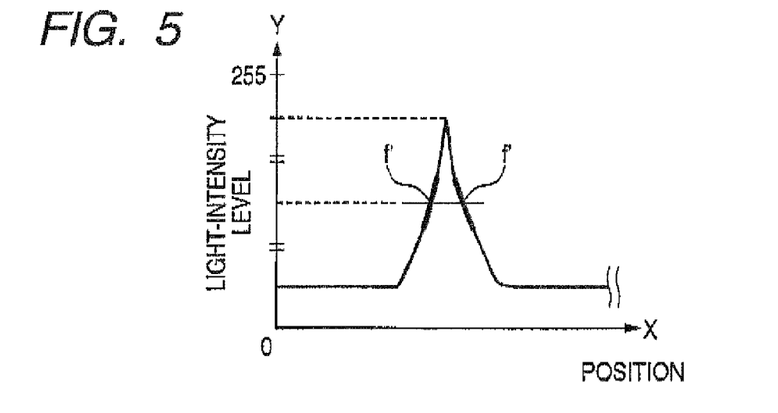
FIG. 5 is a drawing for explaining a method for making a selection based on a differential coefficient f' on a waveform at around an intermediate between the peak and the minimum of the optical-signal luminance level waveform.

Meanwhile, because the waveform signal containing a noise component provides a moderate waveform inclination, the luminance level waveform inclination of an optical signal may be taken into consideration in adjusting the imaging gain. As a method for determining a waveform inclination, a method can be considered that makes a selection based on a waveform differential coefficient f' at around an intermediate between the peak and the minimum of the waveform as shown in FIG. 5. In case the differential coefficient in such a case is adjusted as at least 2 or greater, a sharp-edged waveform (waveform whose noise components are suppressed) is obtained, which further improves the measurement accuracy. Incidentally, although light noise possibly increases in detection because of the difference of the reflection characteristics at the crystalline lens, the vitreous body, etc., due to the wavelength of measurement light, it is effective, in such a case, to adjust the imaging gain as in the above in respect of enhancing the measurement accuracy.

Incidentally, although the image position can be detected from the peak, as described above, measurement result is easy to stably obtain by detecting, as the image position, a waveform intermediate at the threshold S obtained by subtracting a predetermined luminance level from the peak. When setting the threshold S, variation increases at a threshold excessively close to the peak. When the threshold S is excessively low, variation possibly increases under the influence of light noise. It is preferred to take a position where those are avoided.

Incidentally, the SLD having a center wavelength of 850 to 940 nm is applicable as a light source for an ophthalmic apparatus adapted to acquire the characteristic of the patient's eye using low coherent light, e.g. optical coherence tomography (OCT) making use of an optical coherence tomographic technique. Conventionally, there is a problem that the light from a light source is to be inconveniently viewed during acquiring an ocular characteristic. (For example the case of the OCT, since the OCT has a structure that the light emitted from its SLD light source is scanned in up, down, left and right directions, the patient is to troublesomely view, the scanning of light.) Against such a problem, the use of an SLD having a center wavelength of 850 to 940 nm allows the patient not to conscious about the light from the light source, thus relieving the burden on the patient and hence obtaining an ocular characteristic with accuracy. When the OCT uses an SLD having a center wavelength of 850 to 940 nm, the lower of resolution is to be considered as compared to the case using an SLD having a center wavelength of around 830 nm. In such a case, it is satisfactory to use an SLD having a broad half bandwidth in order to supplement the lowering of resolution.

Now explanation is made on a second embodiment using an eye refractive power measurement apparatus according to the invention. Note that the optical and control systems are similar to those shown in FIG. 1, and hence omitted to explain. This embodiment explains a method to determine refractive power of the eye E by adding together the pieces of image data obtained by a plurality of times of imaging, Note that, in this embodiment, adding process is taken once to twice. In this case, the imager device 22 is caused to take ring pattern images successively, to store a plurality of image data for adding process in the frame memory 71. Here, the imager device 22 has an image pickup time, e.g. 1/30 second, at one time. By performing imaging at a predetermined interval (at an interval of 1/30 second in the embodiment), the image data obtained is successively outputted to the frame memory 71. In the embodiment, the ring-pattern images thus picked up are represented by a first image, a second image and a third image in the order of imaging for the explanation. Incidentally, the frame memory 71 is to store image data, represented as luminance levels of 0-255 on a pixel-by-pixel basis due to imaging at the imager device 22.

Figure 6A:
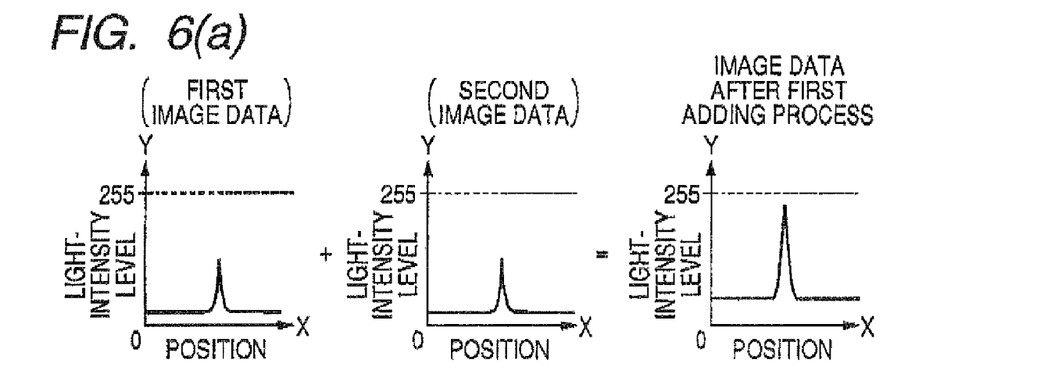
FIG. 6 is a drawing for explaining an adding process.
Figure 6B:
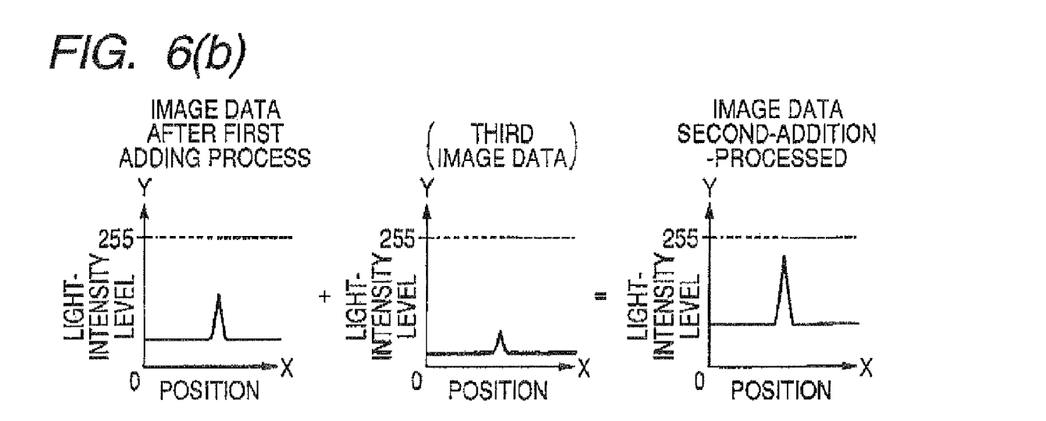
Figure 7:
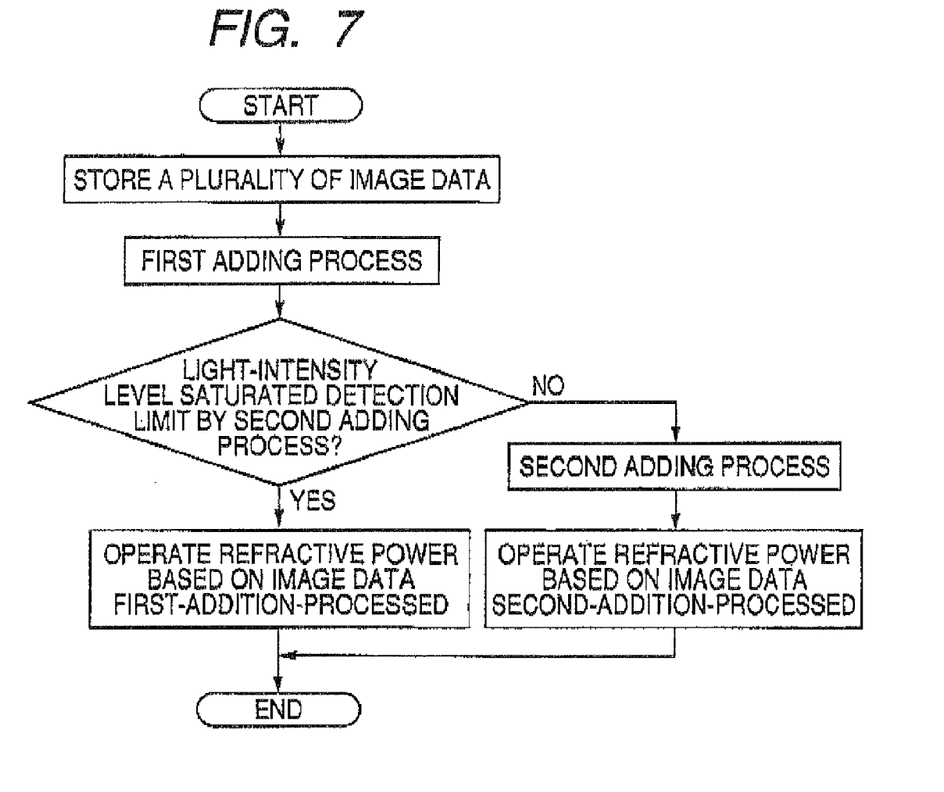
FIG. 7 is a flowchart for explaining the adding process.

At first, the control section 70 performs first adding process on the first image data and the second image data (see FIG. 6A). Furthermore, the control section 70 performs second adding process on the image data on which the first adding process was done and the third image data (see FIG. 6B). In this embodiment, determination is made as to whether or hot the optical signal based on/the addition-processed image data has a luminance, level saturates a detection limit, and the number of times of adding process depending is controlled upon the determination result (see FIG. 7). Namely, in the case the image data on which the second adding process was done has an optical-signal luminance level having a peak completely saturated, refractive-power operation is made based on the image data the first adding process was done. Incidentally, adding process refers to a processing to sum up the luminance levels of different ones of image data with their coordinates made coincident.

When operating refractive power based on a measurement image (ring pattern image) after the adding process, there is no need to obtain a measurement result based on the single imaging. Accordingly, the light amount at the light source 11 and the imaging gain can be set to small values as compared to the case to obtain a measurement image at single imaging. By setting up the measurement light amount and imaging gain lower, light noise can be suppressed furthermore. Although the embodiment is structured to perform the adding process after storing in the frame memory 71 a plurality of obtained image data through the imager device 22, the adding process may be performed by superposing the image data obtained later over the same memory area as that of the image data already stored in the frame memory 71.

Figure 8:
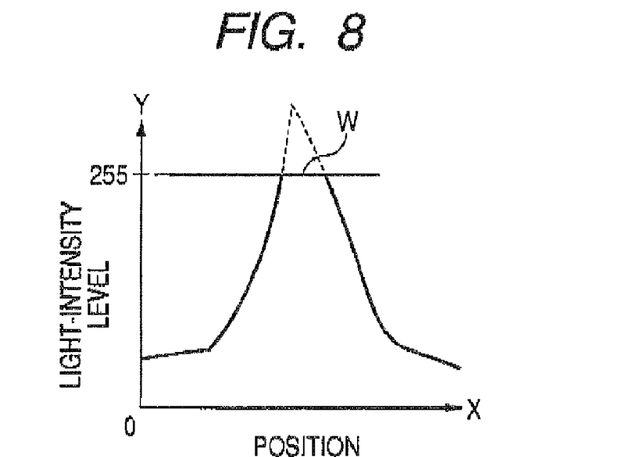
FIG. 8 is a drawing showing an excessive saturation of the optical-signal luminance level.
Figure 9:
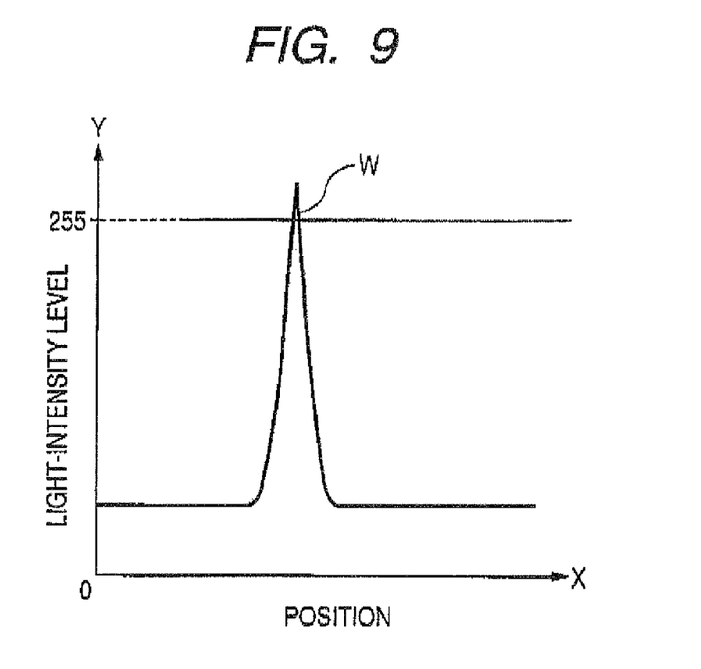
FIG. 9 is a drawing showing a slight saturation of the optical-signal luminance level.

Meanwhile, with a structure in which the addition-processed image data obtained immediately before an excessive saturation of the optical-signal luminance level is used the image data for use in operating refractive power, contrast is made more clear between the ring pattern image itself and the noise component, thus enhancing the measurement accuracy. Note that, if the optical-signal luminance level is saturated excessively by a plurality of times of adding process, the resulting image position is detected containing an increased amount of noise components, thus having an adverse effect upon the measurement accuracy (see FIG. 8). Nevertheless, when the luminance level waveform of the optical signal is in a degree slightly saturated (saturated at the peak but saturation area is slight in amount), noise components are less contained in such a degree as having an effect upon the measurement accuracy. Note that, in order to determine whether slightly saturated or excessively saturated, a determination may be made as to whether or not the number of pixels, corresponding to the area where the optical-signal luminance level is saturated in a predetermined meridional direction, (i.e. width range W in FIGS. 8 and 9) exceeds a predetermined allowable range (allowable number).

Although in the embodiment, the adding process is performed once to twice, the structure is also applicable to the case that the adding process is performed trice or more.

Incidentally, when measuring a patient whose fundus is less reflective of light, the light source 11 may be structured to output an increasing amount of light. In such a case, light amount may be increased depending upon the peak of a light-amount level distribution of the first image data. This enables refractive power measurement even on the patient whose fundus is less reflective of light.

Figure 10A:
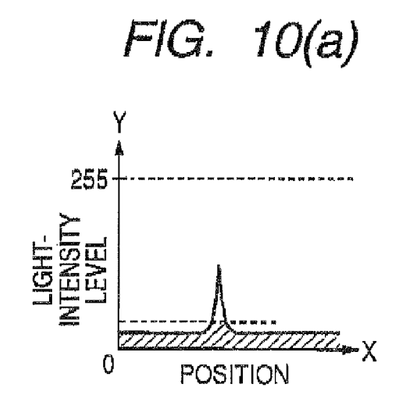
FIG. 10 is a drawing for explaining a subtracting process.
Figure 10B:
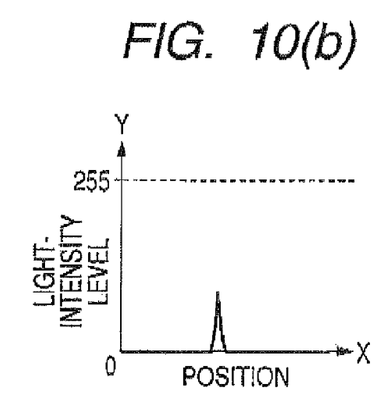

As a modification of the second embodiment, it is possible to add together the pieces of image data that are previously removed of noise components by performing a subtracting process for the pieces of image data obtained by imaging. FIG. 10A shows a luminance level, waveform of the optical, signal of the first image data. Here, the control section 70 performs the process for subtracting a low luminance level component (hatched area) from the image data. This can remove noise components from the periphery of the ring pattern image. FIG. 10B shows a luminance level waveform of an optical signal subtraction-processed. Likewise, by adding together the second and third images of data previously subtraction-processed, the adding process can be made in the state that noise is removed, thus avoiding the effect of measurement errors furthermore.

Incidentally, the adding process is used in the embodiment. Alternatively, by using the imager device 22 in which storage time of an optical signal is variable and a long storage time is possible, the ring pattern image may be imaged in a state that the storage time of the image per imaging is set to a predetermine time (e.g. 100 ms a time) and the light amount of the light source 11 and the imaging gain of the imaging device 22 that constitute a factor to cause light noise are set low. In such a case, in order to obtain a measurement image of immediately before saturation, the operation control section 70 may be configured to analyze an optical-signal luminance level in a predetermined meridional direction of the image data at the time of imaging the ring pattern image, to repeat the imaging while increasing the storage time if the peak thereof is low, and to determine, when a predetermined measurement image is obtained, the refractive power depending upon the predetermined measurement image. Meanwhile, if the ring pattern image is excessively saturated, the imaging may be repeated while gradually decreasing the storage time so that, when a predetermined measurement image is obtained, the refractive power can be determined depending upon the predetermined measurement image.

The invention claimed is:

1. An eye refractive power measurement apparatus for objectively measuring eye refractive power of a patient's eye, comprising:
   a light-projecting optical system that includes a light source and projects measurement light onto a fundus of the patient's eye;
   a light-receiving optical system that includes an imager device serving as a two-dimensional light-receiving element and receives the measurement light reflected from the fundus; and
   an operating section that determines the eye refractive power of the eye based on a two-dimensional pattern image by the measurement light imaged by the imager device,
   wherein the light source is a super-luminescent diode or a laser diode that emits light having a center, wavelength in a range of approximately 850 nm to 940 nm.

2. The eye refractive, power measurement apparatus according to claim 1, wherein an imaging gain of the imager device is set based on a wavelength range of the light to be emitted by the light source and a wavelength sensitivity characteristic of the imager device so as to obtain from the two-dimensional pattern image an optical signal required for determining the eye refractive power and to suppress an noise-component optical signal from being contained in the two-dimensional pattern image.

3. The eye refractive power measurement apparatus according to claim 2, wherein
   the two-dimensional pattern image is a ring pattern image, and
   the imaging gain of the imager device is set to suppress the noise-component optical signal from being contained in an inner region of the ring pattern image.

4. The eye refractive power measurement apparatus according to claim 2, wherein the imaging gain of the imager device is set so that an optical signal obtained from the two-dimensional pattern image includes a waveform assuming symmetric left and right on the border of a peak thereof.

5. The eye refractive power measurement apparatus according to claim 1, wherein the operating section determines the eye refractive power based on a result of an adding process of respective optical signals obtained from a plurality of two-dimensional pattern images as viewed at the same patient's eye.

6. The eye refractive power measurement apparatus according to claim 5, wherein the operating section sums up the respective optical signals from which a predetermined signal component is subtracted.

7. The eye refractive power measurement apparatus according to claim 5, wherein the operating section determines whether or not a level of the summed-up optical signal saturates a detection limit.

* * * * *